(12) United States Patent
Szymaitis et al.

(10) Patent No.: US 12,636,315 B2
(45) Date of Patent: May 26, 2026

(54) METHOD FOR TREATING PERIODONTAL DISEASE

(71) Applicant: Dennis W. Szymaitis, Pittsburgh, PA (US)

(72) Inventors: Dennis W. Szymaitis, Pittsburgh, PA (US); Josephine Yvorra, Pittsburgh, PA (US)

(*) Notice: Subject to any disclaimer, the term of this patent is extended or adjusted under 35 U.S.C. 154(b) by 275 days.

(21) Appl. No.: 18/491,880

(22) Filed: Oct. 23, 2023

(65) Prior Publication Data

US 2025/0127808 A1 Apr. 24, 2025

(51) Int. Cl.
| | |
|---|---|
| A61K 33/42 | (2006.01) |
| A61C 19/06 | (2006.01) |
| A61K 9/14 | (2006.01) |
| A61K 45/06 | (2006.01) |
| A61P 1/02 | (2006.01) |

(52) U.S. Cl.
CPC ............ *A61K 33/42* (2013.01); *A61C 19/063* (2013.01); *A61K 9/14* (2013.01); *A61K 45/06* (2013.01); *A61P 1/02* (2018.01)

(58) Field of Classification Search
None
See application file for complete search history.

(56) References Cited

U.S. PATENT DOCUMENTS

| | | | | |
|---|---|---|---|---|
| 5,017,627 A | * | 5/1991 | Bonfield | ................. A61L 27/46 623/23.61 |
| 5,037,543 A | | 8/1991 | Maejima et al. | |
| 5,462,722 A | | 10/1995 | Liu et al. | |
| 7,105,182 B2 | | 9/2006 | Szymaitis | |
| 2006/0292089 A1 | | 12/2006 | Szymaitis | |
| 2016/0317712 A1 | | 11/2016 | Sereno et al. | |
| 2019/0125872 A1 | | 5/2019 | Szymaitis | |
| 2023/0038764 A1 | | 2/2023 | Zhang et al. | |

FOREIGN PATENT DOCUMENTS

| | | |
|---|---|---|
| CN | 104446431 A | 3/2015 |
| EP | 1464345 A2 | 10/2004 |

OTHER PUBLICATIONS

Vivekanand Sabanna Kattimani, et al., "Hydroxyapatite—Past, Present, and Future in Bone Regeneration", Libertas Academica, Bone and Tissue Regeneration Insights, pp. 9-19, 2016:7.
International Search Report for PCT/US2024/052349 dated Jan. 15, 2025.
Written Opinion of the International Searching Authority for PCT/US2024/052349 dated Jan. 15, 2025.

* cited by examiner

*Primary Examiner* — Bong-Sook Baek
(74) *Attorney, Agent, or Firm* — Buchanan Ingersoll & Rooney PC

(57) ABSTRACT

A method of treating periodontal disease is disclosed in which a composition of a fluid and hydroxyapatite particles are placed in the periodontal pocket. The hydroxyapatite particles have a normal particle size distribution. At least 90% of the hydroxyapatite particles have a particle size smaller than 50 μm and a particle size median is between 2.5 μm and 19.4 μm. Preferably the fluid is water or saline present in a sufficient amount to act as a wetting agent and to form a paste.

11 Claims, 4 Drawing Sheets

Brand B, Lot 2

Brand C

METHOD FOR TREATING PERIODONTAL DISEASE

FIELD OF THE INVENTION

The invention relates to a method of treating periodontal disease by placing in the periodontal pocket a composition containing hydroxyapatite.

BACKGROUND OF THE INVENTION

Periodontal disease occurs when bacteria colonize the sulcus space between the teeth and gingiva. The bacteria cause inflammation. The inflammation destroys the gingival epithelial lining and attachment apparatus to the tooth. The inflammation then progresses down the tooth root toward the apex of the root and destroys periodontal structure and bone. As periodontal disease progresses open pockets develop between the tooth and the gingiva. A dentist can determine the presence and extent of periodontal disease using a probe to measure the depth of pockets between each tooth and gingiva. X-rays can reveal the extent of any bone loss.

In orthopedic surgery and dental applications, there is a great need for biocompatible and bioresorbable implant materials which can be used as a bone substitute. This includes bone lost due to periodontal disease, ridge augmentation, bone defect or bone cavities due to trauma or surgery, and spinal fusion. After implantation, the bone substitute is resorbed and replaced by the formation of new bone.

In orthopedic surgery, autogenous bone has been used quite often for bone repair or bone substitute. Autogenous bone has good biocompatibility, is not subject to immunological rejection, and induces bone growth. However, it requires a secondary surgery and thus increases the burden on the patient while delaying recovery. On the other hand, both allograft bone from other human sources and xenograft bone from animal sources often suffer the disadvantages of adverse immunological reactions. This will result in an inflammatory reaction and rejection after implantation.

The major inorganic composition of hard tissue is a calcium phosphate compound called biological apatite. Bone has 65% to 70% of biological apatite and teeth contain near 98% biological apatite. Hydroxyapatite and other apatite compounds have the same crystal structure as biological apatite. In principle, these apatite materials should be ideal candidates for bone replacement. Hydroxyapatite particles can be created by reacting calcium sulfate in a calcium chloride solutions and precipitating those particles from the solution. However, as Lui et al. report in U.S. Pat. No. 5,462,722 "the precipitated hydroxyapatite and other apatite compounds have very fine particle size. The difficulty in manipulating these fine powders renders them useless as materials for bone replacement." Consequently, Lui et al. disclose a method of creating a bone substitute material which is a composite of calcium phosphates formed on the exterior surface of a calcium sulfate particle.

U.S. Pat. No. 7,105,182 to Szymaitis, as well as his U.S. Patent Application Publication No. 2006/0292089 and related European Patent No. EP 1 464 345 disclose a periodontal structure regeneration composition for the treatment of periodontal disease and method of treating periodontal disease using that composition. The composition is a mixture of a commercially available naturally occurring type of collagen and particles of a bone growth material. The bone growth material may be human bone particles, hydroxyapatite, bovine bone particles, ground coral, or calcium sulfate. The composition is used without incisions to regenerate the periodontal structure lost to periodontal disease. The European patent also contains a review of the relevant literature concerning bone re-growth and osteoinductive compositions.

The Szymaitis patents and published applications teach that the composition provides a support for growth of new bone and adjacent soft tissue. These references teach that the collagen captures the bone growth material so that the bone growth material remains in place in the periodontal pocket. Other references disclose different materials that are injected into the periodontal pocket to provide a scaffold that supports growth of new bone and adjacent soft tissue.

The Szymaitis patent and published applications contain data showing that improved healing occurs only when the composition contains one type of collagen called free collagen which is not cross-linked. There are also a number of publications that report results of studies involving the use of nanoparticles of hydroxyapatite. Those studies have consistently found that the use of nanoparticles of hydroxyapatite does not improve healing. Some studies conclude that nanoparticles of hydroxyapatite do not remain at the site of damaged bone long enough to affect healing. Consequently, the art has believed that the application of hydroxyapatite without another material that will keep this bone growth material in place will not improve healing.

SUMMARY OF THE INVENTION

We treated several patients with the composition disclosed in the Szymaitis patents and published applications and observed improved healing. We also treated patients having periodontal disease by placing in the periodontal pocket a paste containing only hydroxyapatite and water or saline. We used three different brands of hydroxyapatite which we identify here as Brand A, Brand B and Brand C. All of these materials were in powder form. For each patient we added a sufficient amount of water or saline to the hydroxyapatite particles to form a paste and placed the paste in the periodontal pocket using a syringe. We observed that the paste covered the portion of the tooth which had experience bone loss. Patients treated with Brand A hydroxyapatite and Brand B hydroxyapatite had healing comparable to patients who had been treated with the free collagen and hydroxyapatite mixture disclosed in the Szymaitis patents and published patent applications. But patients treated with the Brand C hydroxyapatite did not have that improved healing. Consequently, we conducted many tests on the three brands of hydroxyapatite to determine why two brands provided improved healing and one did not. We found that the sizes of the hydroxyapatite particles and the distribution of those particle sizes is responsible for the improved healing.

Only the compositions containing hydroxyapatite particles having a normal particle size distribution, at least 90% of the hydroxyapatite particles having a particle size smaller than 50 µm and a particle size median is between 2.5 µm and 19.4 µm provided improved healing.

DESCRIPTION OF THE PREFERRED EMBODIMENTS

Figure 1:
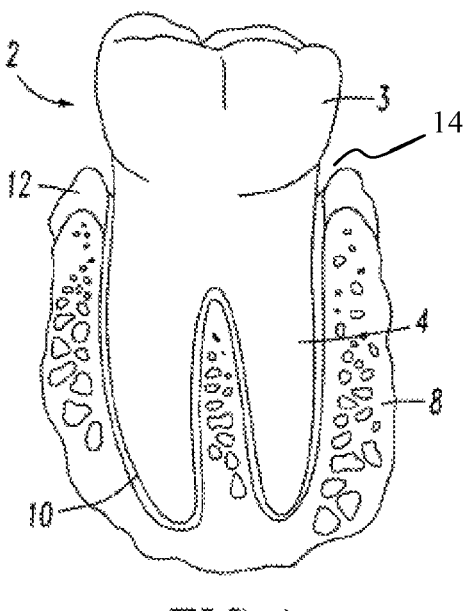
FIG. 1 is a front view of a healthy tooth.
Figure 2:
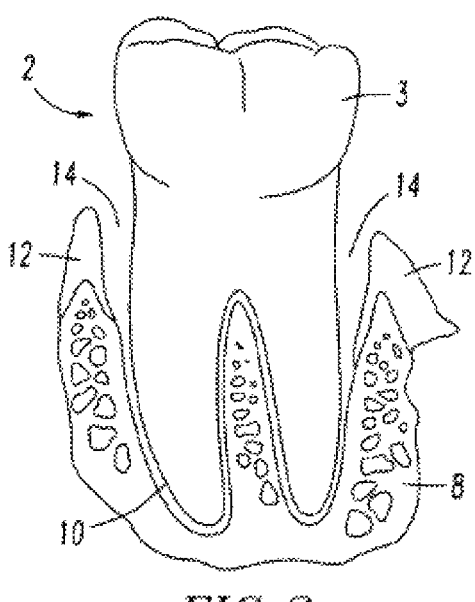
FIG. 2 is a front view of a tooth in a patient experiencing periodontal disease.
Figure 3:
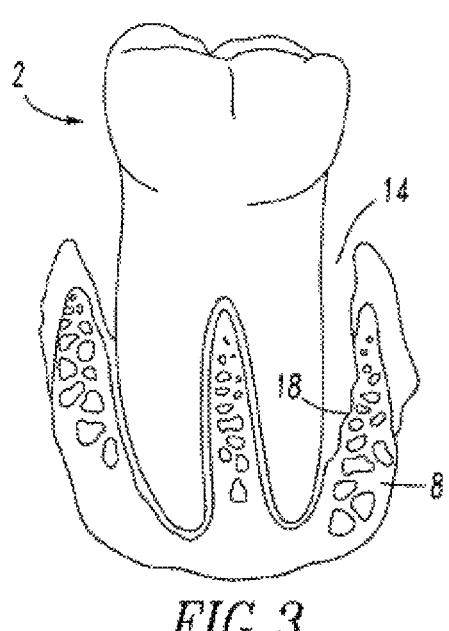
FIG. 3 is a front view of a tooth in a patient having advanced periodontal disease and bone loss.

As can be seen in FIG. 1 a tooth 2 has a crown 3 and root 4. The alveolar bone 8 surrounds the root 4. There is a periodontal ligament 10 around much of the root 4 and gingiva 12. The periodontal ligament 10 surrounds the upper part of the root 4 and the base of the crown 3. There is a pocket 14 between the gingiva 12 and the tooth 2. In a healthy tooth shown in FIG. 1 this pocket 14 is very shallow, typically one to three millimeters. Bacteria colonize the pocket. The bacteria cause the pocket 14 to deepen as shown in FIG. 2. As periodontal disease progresses the bacteria cause inflammation that destroys the ligament and bone creating depressions 18 in the bone shown in FIG. 3.

Figure 4:
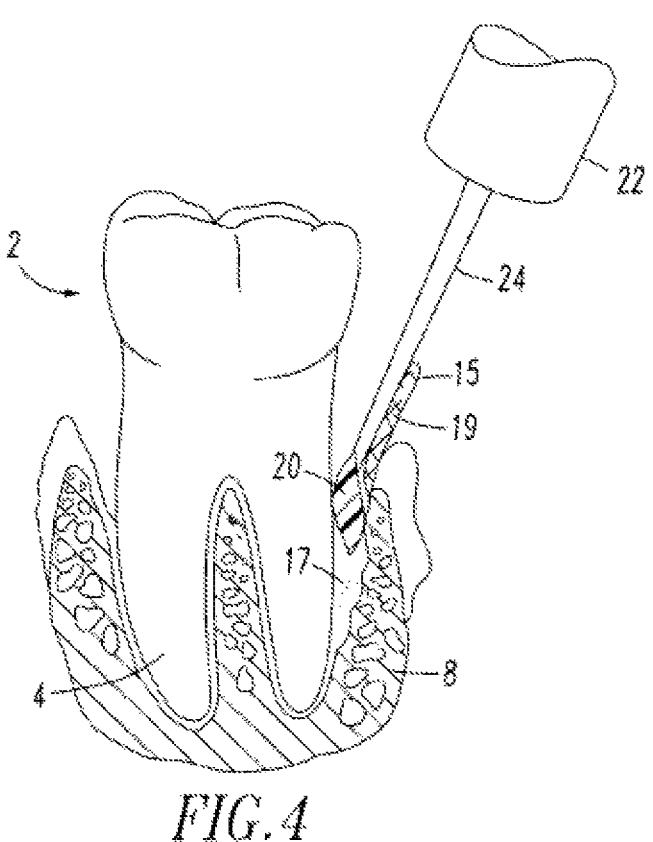
FIG. 4 is a front view of the diseased tooth of FIG. 3 being treated in accordance with the present invention.

Standard periodontal practice is to completely clean the pocket of all abraded bone and to remove all granulation tissue. However, we prefer to leave the granulation tissue in the pocket. To abrade the root and gingival surfaces we simply place the dental bur into the pocket, but do not incise the gums. After abrading, specially designed gauze 15, shown in FIG. 4 is placed into the 1-1.5 mm created space to both distend the pocket and create hemostasis with or without chemicals. We prefer to provide three sizes of gauze strips of 5 mm, 7.5 mm and 10 mm wide and 10 cm in length. As an additional use, the gauze can carry and place antibacterial materials, antibiotics, or any type of root conditioning materials. These materials include epinephrine, alum, aluminum sulfate, aluminum, potassium sulfate, collagen, aluminum chloride, and oxyguinol sulfate as well as antibacterial chemicals peroxide, chlorhexidine, chlorhexidine iodine and triiodomethane. Sufficient time is allowed for hemostasis, distention, and the placed materials to function as designed, then the gauze 15 can be removed.

As shown in FIG. 4, after abrading we inject a composition 20 into the pocket 14 through a syringe 22 and needle 24. This composition contains a fluid and hydroxyapatite particles. The hydroxyapatite particles used in our method have a normal, sometimes called standard, particle size distribution. At least 90% of the hydroxyapatite particles have a particle size smaller than 50 μm and a particle size median is between 2.5 μm and 19.4 μm. A median is a particle size where half of the particles in the composition have a particle size above this value and half the particles in the composition have a size below this value.

There is a sufficient amount of fluid in the composition so that the composition is a paste or gel. We prefer to use water or saline as the fluid which can be used in small amounts to form a paste. However, any biocompatible liquid that acts as a wetting agent can be used. Polyethylene glycol, hyaluronic acid and poly (hydroxyethyl methacrylate) are fluids that can be used to make the composition a gel.

Figure 5:
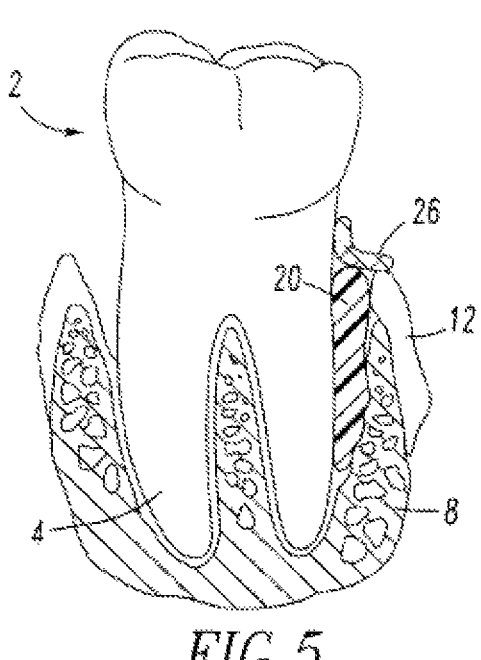
FIG. 5 is a front view of the diseased tooth of FIG. 3 immediately after completion of a treatment in accordance with one embodiment of the present invention.

Sufficient composition 20 is injected to fill the pocket as shown in FIGS. 4 and 5. The gingiva 12 then rebounds from the distension and moves back toward the tooth. Less than 0.1 cc of paste would usually be injected into a pocket for two molars. The paste is placed in the space between the root and granulation tissue. The paste was positioned as a layer less than 1 mm thick on the root. There may be small gaps in the layer in the periodontal pocket. But such gaps do not affect healing.

Because the composition is injected into the periodontal pocket through a needle the viscosity has to be sufficient to pass through the needle but viscous enough to remain in the pocket. Some composition is forced from the pocket when the gingiva rebounds or returns to its normal position. But most of the composition remains in the pocket. However, the viscosity of the composition that allows easy passage through the needle enables further migration from the periodontal pocket during normal movement of the mouth. The fluid may contain a thickener when the fluid is added to the hydroxyapatite particles. One or more growth factor, nutrient factor, drug, anti-inflammatory agent, anti-bacterial agent, antibiotic, calcium containing compound, root treatment material, bone morphogenic protein, dental matrix derivative or combination of these materials may be placed in the periodontal pocket before, during or after placement of the hydroxyapatite particles.

We prefer to apply an adhesive 26 over the pocket to eliminate any pain or discomfort, to stop any bleeding, to keep the regeneration material in place, and to prevent foreign material from entering the pocket and dislodging the regeneration material. However, we have found that bone regeneration and healing occurs even when no adhesive is used. We prefer to use butyl cyanoacrylate as the adhesive because this material cures with water. Another suitable water curable adhesive is 2-Octyl Cynoacrylate sold by Johnson & Johnson under the trademark DERMABOND. One could also use an adhesive that cures when exposed to light. Dentistry now uses polymers for filling cavities that cure when exposed to blue light. There are also adhesives that cure when exposed to ultraviolet light that could be used. However, far too many eye injuries caused by ultraviolet light have resulted in a general reluctance to use ultraviolet light in dentistry. There are adhesives that cure upon exposure to visible light which should be useful in this procedure. Other water curable adhesives, auto-curing adhesives, heat cured adhesives and reactive-component cure adhesives may also be acceptable We treated several patients suffering from periodontal disease by injecting into the periodontal pockets of the patient a paste containing one of Brand A hydroxyapatite, Brand B hydroxyapatite or Brand C hydroxyapatite combined with water or saline. Two lots of Brand B hydroxyapatite were used which we identify as Brand B, Lot 1 and Brand B, Lot 2. Granulation tissue remained in the periodontal pockets of all patients when the paste was injected. The paste covered the portion of the tooth which had experienced bone loss. Data from several of these patient treatments are presented and discussed later in this specification. Patients treated with Brand A hydroxyapatite and Brand B hydroxyapatite had healing comparable to patients who had been treated with the free collagen and hydroxyapatite mixture disclosed in the Szymaitis patents and published patent applications. But patients treated with the Brand C hydroxyapatite did not have that improved healing.

We conducted several tests of the Brand A hydroxyapatite, Brand B, Lot 1, hydroxyapatite, Brand B, Lot 2, hydroxyapatite and Brand C hydroxyapatite to identify differences among properties which could account for the fact that the Brand A hydroxyapatite paste, and the Brand B hydroxyapatite paste improved healing while the Brand C hydroxyapatite did not. Electron micrographs of samples of each of Brand A hydroxyapatite, Brand B, Lot 1, hydroxyapatite, Brand B, Lot 2, hydroxyapatite and Brand C hydroxyapatite did not show any significant differences among the three brands of hydroxyapatite. There was no significant difference among the three brands in clotting or antibacterial properties. Tests to determine the crystalline structure of the three brands of hydroxyapatite did not show any significant disease as the Brand A hydroxyapatite we used to treat patients. Similarly, we can expect that any sample of Brand B hydroxyapatite having a Median particle size distribution within the Median Range reported in Table 1 for Brand B hydroxyapatite will have the same properties and provide the same result when used to treat periodontal disease as the Brand B hydroxyapatite we used to treat patients. Finally, we can expect that any sample of Brand C hydroxyapatite having a Median particle size distribution within the Median Range reported in Table 1 for Brand C hydroxyapatite will have the same properties and provide the same result when used to treat periodontal disease as the Brand C hydroxyapatite we used to treat patients.

TABLE 1

| | | Particle Size Comparison | | |
| --- | --- | --- | --- | --- |
| | Brand A | Brand B, Lot 1 | Brand B, Lot 2 | Brand C |
| Up to 10% | 2.414 μm | 1.1524 μm | 3.5702 μm | 0.7255 μm |
| Up to 20% | 3.636 μm | | | |
| Up to 30% | 5.278 μm | | | |
| Up to 50% | 10 μm* | 4.0831 μm | 18.4194 μm | 1.4612 μm |
| Up to 90% | 49.018 μm | 13.7019 μm | 39.6447 μm | 2.6410 μm |
| Mean | 24.215 μm | 6.0353 μm | 20.7417 μm | 1.5999 μm |
| Median | 10.786 μm | 4.0831 μm | 18.4194 μm | 1.4612 μm |
| Range of | 591.4 μm | 39.084 μm | 116.084 μm | 6.57 μm |
| particle sizes | 1 to 592.4 μm | 0.15 to 39.234 μm | 0.15 to 116.21 μm | 0.15 to 6.72 μm |
| Span | 4.3200 | 3.0735 | 1.9585 | 1.3122 |
| Median Range | 8.626 to 12.946 | 2.5464 to 5.6818 | 17.4402 to 19.3986 | 0.8051 to 2.1123 |

Figure 6:
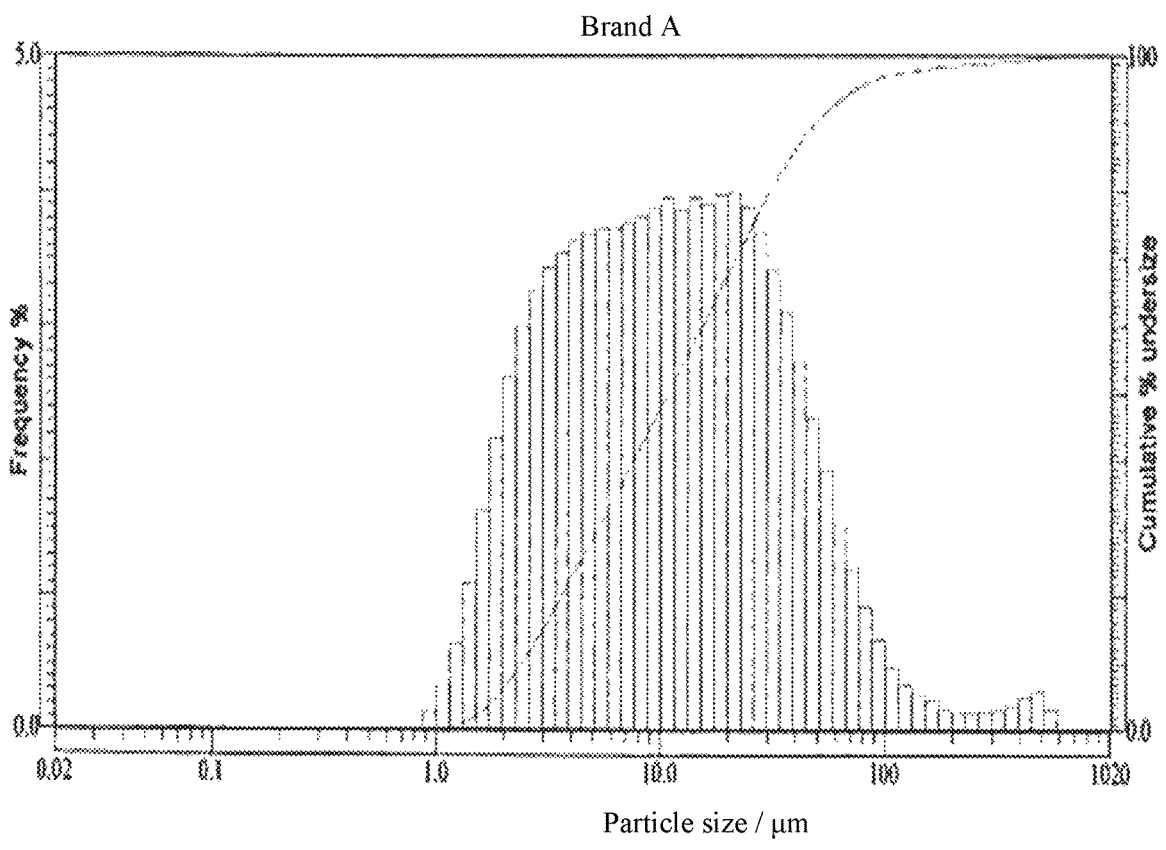
FIG. 6 is a graph showing the particle size distribution in a sample of Brand A hydroxyapatite that was used to treat patients.
Figure 7:
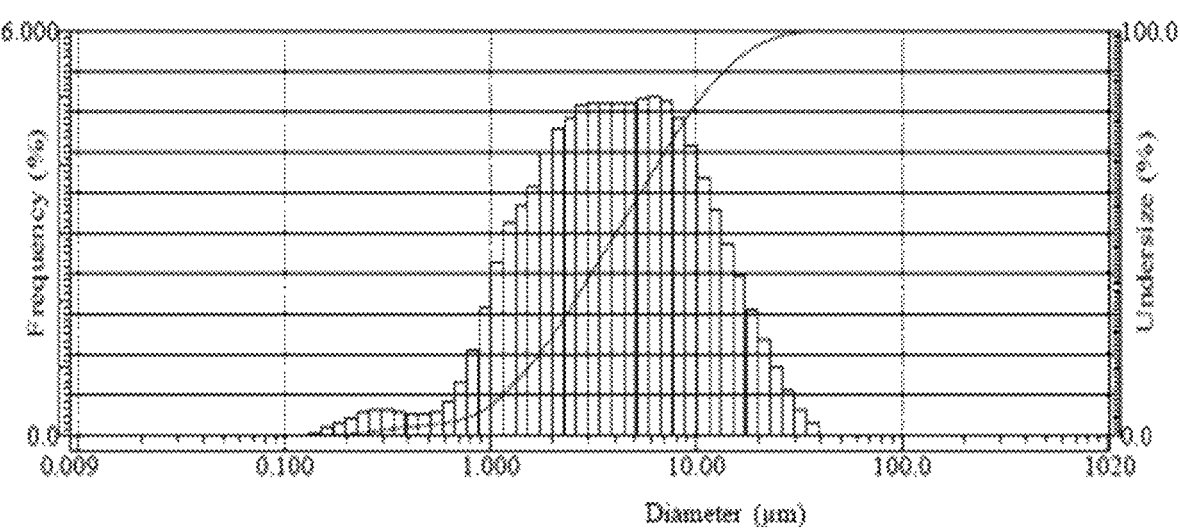
FIG. 7 is a graph showing the particle size distribution in a sample of one lot of Brand B hydroxyapatite that was used to treat patients.
Figure 8:
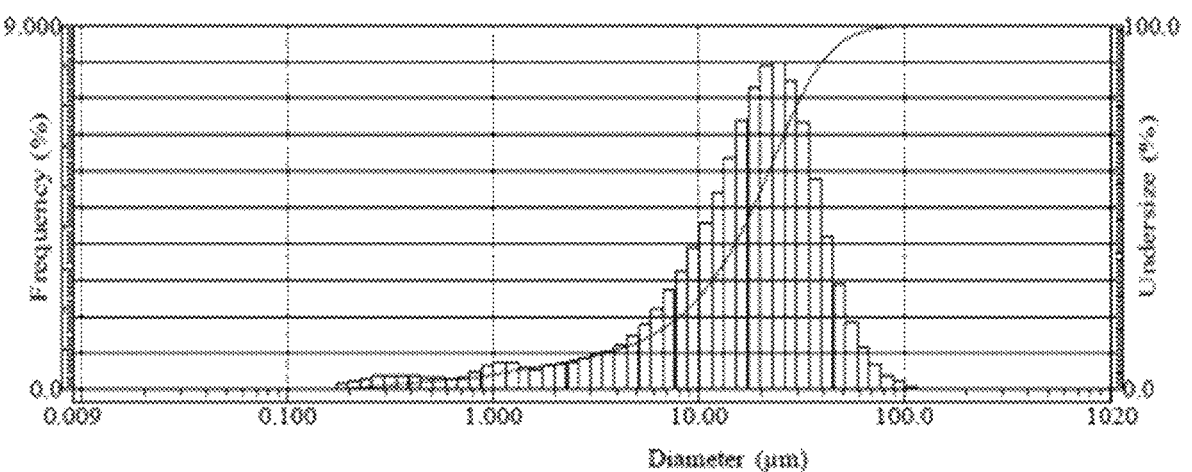
FIG. 8 is a graph showing the particle size distribution in another a second lot of Brand B hydroxyapatite that was used to treat patients.
Figure 9:
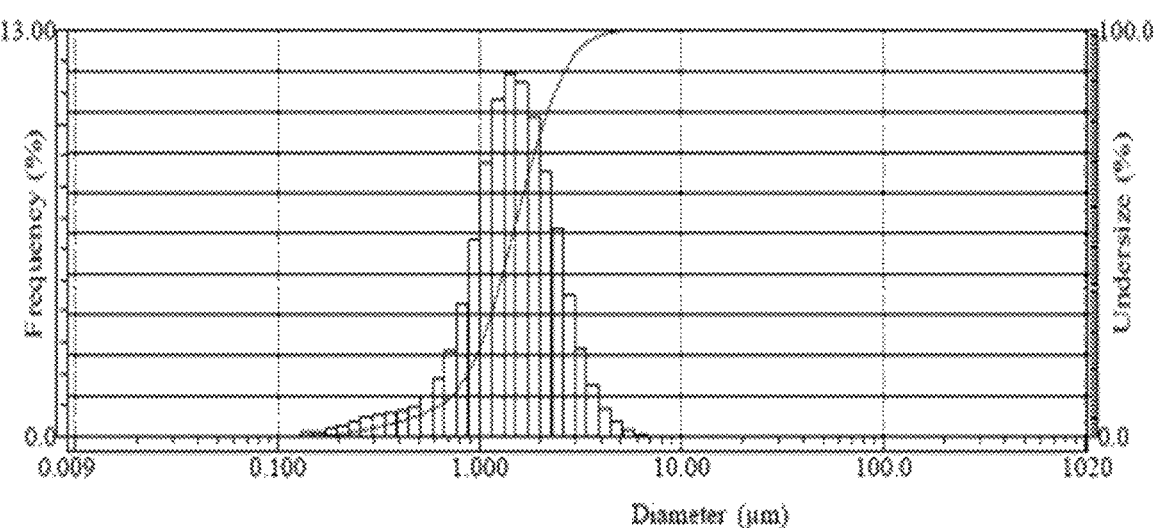
FIG. 9 is a graph showing the particle size distribution in a sample of Brand C hydroxyapatite that was used to treat patients.

*This value was not in the analyzer report but was taken from the graph in FIG. 6 differences. An examination of the porosity of the three brands of hydroxyapatite also did not reveal any significant differences among them. However, there is a significant difference between the particle sizes and the particle size distribution of the hydroxyapatite particles in the Brand C hydroxyapatite and the particle sizes and the particle size distribution of the hydroxyapatite particles in the Brand A hydroxyapatite and the Brand B hydroxyapatite. Those differences can be seen in FIGS. 6, 7, 8 and 9 and Table 1.

One sample of each of Brand A hydroxyapatite, Brand B, Lot 1, hydroxyapatite, Brand B, Lot 2, hydroxyapatite and Brand C hydroxyapatite were analyzed for particle size distribution. Each sample was in the same condition as the material had been used to treat patients. Testing was done on a Horiba LA-910 laser diffraction particle size analyzer. The analyzer generated the graphs FIGS. 6, 7, 8 and 9 and all of the data in Table 1 except for the Median Range.

The Median Range was calculated using the Scan number in the Table 1. Scan is similar to standard deviation and is the distance between the "Up to 10%" particle size number and the "Up to 90%" particle size. According to statistical theory we can say with 95% confidence that the actual Median of any sample of the tested hydroxyapatite material will be within range that is the Median reported by the analyzer plus or minus one half of the Scan. Consequently, the smaller number in each Median Range listed in Table 1 was calculated by subtracting one-half of the Scan from the Median reported by the analyzer for the sample. The larger number in each Median Range listed in Table 1 was calculated by adding one-half of the Scan from the Median reported by the analyzer for the sample. One can expect that any sample of Brand A hydroxyapatite will have a Median particle size distribution within the Median Range stated in Table 1 for Brand A hydroxyapatite, will have the same properties and will provide the same result when used to treat periodontal Comparing the particle size distribution of the Brand C hydroxyapatite with the particle size distribution of the Brand A hydroxyapatite and the Brand B hydroxyapatite we see that in all of the products 90% of the particles are less than 50 μm. But the "Up to 90%" particle size for the Brand C material is about one seventh that of the Brand B, Lot 1 material. The "Up to 90%" particle size for the Brand A material and the "Up to 90%" particle size for the Brand B, Lot 2 material are about twenty or twenty-five times larger than the "Up to 90%" particle size for the Brand C material. The range of particle sizes of the Brand C hydroxyapatite is much smaller than the range of particle sizes in the Brand A hydroxyapatite and the Brand B hydroxyapatite samples. Furthermore, the Median Range for the Brand C hydroxyapatite includes smaller particles and does not overlap the Median Range for the Brand A hydroxyapatite sample or the Brand B hydroxyapatite samples. This data indicates that particle size alone is not a determinant of whether hydroxyapatite will improve healing of periodontal disease. Rather the data indicate that hydroxyapatite particles (i) having a normal particle size distribution, (ii) at least 90% of the hydroxyapatite particles being smaller than 50 μm in size and (iii) the particle size median being between 2.5 μm and 19.4 μm will improve healing of periodontal disease.

We have observed that injecting into a periodontal pocket of a person suffering from periodontal disease a paste of hydroxyapatite particles which meet these requirements speeds healing. Immediately after application of the paste, the gingiva that was sore and bleeding became normal with no bleeding and decreased discomfort. The decrease in symptoms coincides with decreased inflammation. Patients were examined between 10 days and 28 days after treatment. At 10 days post-treatment no hydroxyapatite could be observed. The disappearance of hydroxyapatite indicates that it functions differently than how hydroxyapatite functions when used in conventional bone replacement surgery.

The precise mechanism by which bone regeneration and healing occurred in our patients is not understood. Since the presence of Brand A or Brand B in the periodontal pocket was short-lived and healing is long-lived, then the hydroxyapatite brands that improved healing must function as a key to turn on endogenous regeneration.

In the article "Designing Biomaterials for in Situ Periodontal Tissue Regeneration," published online Sep. 12, 2011 in Wiley Online Library (wileyonlinelibrary.com) the authors teach that endogenous regeneration occurs when the body creates instructive biomaterials, growth factors (GFs) and/or other signaling molecules that stimulate/recruit host endogenous cells, including stem/progenitor cells, to invade an injury site and direct robust extracellular matrix (ECM) synthesis and in situ tissue regeneration. GFs are found either as matrix bound proteins attached to the ECM or as soluble molecules secreted by cells or cleaved from the matrix by certain enzymes or proteases. They are large polypeptides that modulate cellular activities including proliferation, differentiation, migration, adhesion and gene expression and regulate the mechanisms and pathways that govern wound healing and tissue regeneration. It is now well recognized that GFs play crucial roles in the complex cascade of biological events of wound healing, by stimulating chemotaxis and cellular proliferation, by transferring information among cells of the same and different type and their microenvironment, by controlling ECM formation and angiogenesis, by regulating the process of contraction and by re-establishing tissue integrity. GFs initiate their action by binding to specific receptors on the surface of target cells, and their effects are concentration-dependent, often in a complex non-monotonic way. The availability of GFs from the conditioned medium of cultured human cells, their expansion through recombinant technologies and improved understanding of their functions and clinical applications has increased the need for pharmaceutical forms. Unfortunately, although many recombinant GFs are now available for research purposes and some have also been tested in humans, the clinical experience so far has been disappointing.

One explanation of why Brands A and B improved healing while Brand C did not improve healing relates to the range of particle sizes being greater in Brands A and B than in Brand C. Perhaps particles of different sizes of hydroxyapatite bind to growth factors in the body which causes those growth factors to initiate the process of endogenous regeneration. More than one growth factor may be needed to cause tissue regeneration and each factor is activated by a different size hydroxyapatite particle. Alternatively, there may two or more different particle sizes need to activate a growth factor.

Another possible explanation relates to the distribution of particles of difference sizes in a volume of these materials. We know that a selected number of larger hydroxyapatite particles will fill a greater volume than the same number of smaller hydroxyapatite particles. When larger hydroxyapatite particles and smaller hydroxyapatite particles are mixed together, the smaller particles will surround the larger particles filling interstices that would otherwise exist between the larger particles if the smaller particles were not present. Consequently, the addition of smaller particles to the large particles will create a mixture that can fill the same, or nearly the same, volume as the larger particles alone. When the mixture of hydroxyapatite particles having a normal particle size distribution, at least 90% of the hydroxyapatite particles having a particle size smaller than 50 μm and a particle size median between 2.5 μm and 19.4 μm. is placed in a periodontal pocket the smaller particles in the interstices between larger particles will not be absorbed as quickly as the smaller particles that are not in the interstices. It may be that the presence of the smaller particle is primarily responsible for causing the bone to regenerate. In a mixture of larger hydroxyapatite particles and smaller hydroxyapatite particles the larger particles keep smaller particles in the periodontal pocket for a longer period of time, a long enough period of time for significant bone regeneration to occur. Having at least 90% of the hydroxyapatite particles being smaller than 50 μm in size assures that enough small particles are present to improve healing. Requiring that the particle size median being between 2.5 μm and 19.4 μm provides enough larger particles such that enough smaller particles remain in the periodontal pocket long enough to improve healing. Without the presence of the larger hydroxyapatite particles the smaller hydroxyapatite particles would be transported away by bodily fluids or liquids consumed by the patient much more quickly.

Another possible explanation of why only Brands A and B improved healing is the difference in total surface area in any selected volume of these materials. Because Brand C has a greater number of smaller particle the total surface area in any selected amount of these materials is greater for Brand C than for Brand A or Brand B. Surface area is inversely related to reaction time for this type of material. Consequently, Brand C may react too fast to provide healing.

Examples of Patients Treated

In periodontics, a sulcus depth of 1-3 mm is accepted as normal. A 4 mm depth is also considered healthy. For this discussion, the healthy sulcus is defined as 1-4 mm, with 5 mm and above designated diseased.

Where a tooth joins with the gingiva, it forms a normal 1-3 mm deep structure called a sulcus. A 1-4 mm depth range is considered healthy because it is the normal 1-3 mm developmental sulcus plus the $4^{th}$ mm that is healthy and maintained with hygiene.

Periodontal disease damages the bottom of the sulcus and increases the depth to 5 mm and above. As the damage increases the depth, then this region is called a pocket. The amount of depth increase is important because it determines both treatment & prognosis. After treatment, any decrease in depth determines the amount of success.

The standard evaluation of periodontal healing begins with the initial depth as the benchmark. All changes in depth are attributed to the therapy. This evaluation method tends to inaccuracy because it is measuring both normal sulcus+ disease depth, while calling both a pocket. The association of pocket with depth is misleading and results with incorrect evaluation. For example, a patient with a 6 mm pocket that healed to 3 mm is referred to as having 50% healing. A correct portrayal is to subtract the 3 mm normal sulcus from the 6 mm pocket (6 mm-3 mm=3 mm). The difference is the diseased 3 mm structure. A result of 3 mm decrease would now have a 100% healing of disease instead of 50% pocket reduction. This different approach profoundly effects the evaluation of success. The amount of total healing becomes unmistakable. Attaining the goal of repairing damaged tissue is dramatically displayed and becomes understandable to non-professionals.

This approach to measure healing of the diseased pocket is used on the following patient examples.

Patient #1: Male 45 Years Old Treated with Brand A Hydroxyapatite Paste

Periodontal disease was isolated to three posterior quadrants with molar furcation involvement. This is a demonstration of the ability of the hydroxyapatite paste to heal a range of furcations. Furcation involvements were 3 of Class I, 4 of Class II, and 1 of Class III. Current therapy is unpredictable with furcation healing uncommon.

The following table reports the number of pockets for each depth at pre-treatment, and post-treatment results for patient #1.

|  | 5 mm | 6 mm | 7 mm | 8 mm | 9 mm | 10 mm |  |
|---|---|---|---|---|---|---|---|
| Pre-Treatment | 30 | 24 | 14 | 1 | 0 | 2 | Total 136 mm diseased pockets |
| Post-Treatment | 6 | 1 | 0 | 0 | 0 | 0 | Total 8 mm diseased pockets |

This patient experienced 94% healing.
13% improved
63% healed

| Furcation Involvement | Class I | Class II | Class III |
|---|---|---|---|
| Pre-Treatment | 3 | 4 | 1 |
| Post Treatment Class 0* | 3 | 2 | 0 |
| Class II | 0 | 2 | 1 |

*Class 0 designates healed

These furcation results are common to the majority of patients treated with Brand A hydroxyapatite. Class I furcations almost always heal. About 66% Class II furcations healed. Class III furcations have least healing A majority remain Class III; some resolve to Class II and a few heal completely.

Patient #2: Female, 70 Years Old Treated with Brand A Hydroxyapatite Paste

Failure of previous periodontal therapy completed 14 years before this treatment did not rule out this additional therapy. We identified the etiology of the recurrence and corrected it to prevent a repeat failure. Incorrect oral hygiene was the culprit and was overcome by correct training.

Long term success cannot be determined immediately after therapy as this patient demonstrated. The measure for success should a disease-free dentition many years after therapy. This patient is a prime example of longevity being 7 years, 11 months post-treatment. Out of 21 depths on treated teeth, she had 3-1 mm pockets, 9-2 mm pockets, 8-3 mm pockets and 1-4 mm pocket.

The following table reports the number of pockets for each depth at pre-treatment, and post-treatment results for patient #2.

|  | 5 mm | 6 mm | 7 mm | 8 mm | 9 mm | 10 mm |  |
|---|---|---|---|---|---|---|---|
| Pre-Treatment | 6 | 8 | 2 | 5 | 0 | 0 | Total 48 mm of diseased pockets |
| Post-Treatment | 0 | 0 | 0 | 0 | 0 | 0 | Total 0 mm of diseased pockets |

This patient experienced 100% healing.

| 100% healed | |
|---|---|
| Furcation Involvement | Class III |
| Pre-Treatment | 1 |
| Post Treatment Class 0 | 1 |

Patient #3 Male, 70 Years Old Treated with Brand A Hydroxyapatite Paste

Periodontal therapy was previously done 15 years prior to this treatment. Retreatment or age did not influence treatment planning because healing, bone regeneration, or longevity is not age related. There were no discernable differences in these categories when compared to younger patients. This patient's numerous controlled medical conditions had no effect on healing. Therefore, they do not influence treatment planning. Our office never had a patient that was medically unfit for treatment with hydroxyapatite paste.

Patient #3 had one Class II furcation that remained a Class II and was maintained until his last appointment at age 75. Complete resolution of a furcation to Class 0 is not necessary for a lengthened success. All furcations experience improved bone health just from the substantial inflammation resolution. Improved hygiene has an unrecognized and unrewarded effect on furcation health. This Class II molar was stable and functioned perfectly.

The following table reports the number of pockets for each depth at pre-treatment, and post-treatment results for patient #3.

|  | 5 mm | 6 mm | 7 mm | 8 mm | 9 mm | 10 mm |  |
|---|---|---|---|---|---|---|---|
| Pre-Treatment | 15 | 4 | 12 | 1 | 0 | 0 | Total 63 mm diseased Pockets |
| Post-Treatment | 3 | 0 | 0 | 0 | 0 | 0 | Total 3 mm diseased pockets |

This patient experienced 95% healing.

| 83% healed | | |
|---|---|---|
| Furcation Involvement | Class I | Class II |
| Pre-Treatment | 5 | 1 |
| Post Treatment Class 0 | 5 | 0 |
| Class II | 0 | 1 |

Patient #4: Female, 60 Years Old Treated with Brand A Hydroxyapatite Paste

Advanced dental training is necessary to treat 10 mm pockets or multiple Class II furcations. These have a poor prognosis due to the extensive damage that requires extensive healing. Current bone regeneration techniques use biologics & barriers, each with a substantial material expense. Add that to the cost of delivery by the dentist, and it ceases to be an affordable option. Even if the patient sacrifices to pay for this endeavor, the success rate on advanced damage is in single digits.

Instruments that measure pocket depth stop at 10 mm, because any tooth with 10 mm has a poor prognosis and are usually extracted. Teeth with 10+mm are so weakened that they are never considered for therapy. Class II furcation involved teeth remain weakened and are bypassed from long term treatment planning. Both problems have a poor prognosis that precludes using them as abutments for bridges and restorative.

Brand A hydroxyapatite had a contrary history and successfully healed such weakened teeth. The 10+mm pocket healed and remained at 3 mm for 2 years with 0 mobility. The three Class II furcations healed to Class 0 with 2-3 mm depths. All of these treated teeth are strong and can be utilized for bridges. The procedures and material cost are a fraction of current therapy. There is no need for advanced training because all dentists and hygienists can attain these results with their current dental skills.

The following table reports the number of pockets for each depth at pre-treatment, and results for patient #4 after-treatment with Brand A hydroxyapatite paste.

This patient experienced 96% healing

| | 5 mm | 6 mm | 7 mm | 8 mm | 9 mm | 10 mm | 10+ mm | |
|---|---|---|---|---|---|---|---|---|
| Pre-Treatment | 5 | 3 | 1 | 2 | 0 | 0 | 1 | Total 28 mm diseased pockets |
| Post-Treatment | 1 | 0 | 0 | 0 | 0 | 0 | 0 | Total 1 mm diseased pockets |

| 100% healed | |
|---|---|
| Furcation Involvement | Class II |
| Pre-Treatment | 3 |
| Post Treatment Class 0 | 3 |

Patient #5: Male, 44 Years Old Treated with Brand A Hydroxyapatite Paste

This patient's treatment with Brand A hydroxyapatite was limited to the mandibular arch. All teeth were involved and demonstrated that this treatment functions equally well on single root anterior teeth and on multiple root posterior teeth. The anterior teeth were surrounded with 5-6 mm and healed to 1-3 mm. Posterior teeth were similar with four 7 mm and two Class II furcations. Pockets resolved with only one 5 mm remaining.

The following table reports the number of pockets for each depth at pre-treatment, and post-treatment results for patient #5.

| | 5 mm | 6 mm | 7 mm | 8 mm | 9 mm | 10 mm | |
|---|---|---|---|---|---|---|---|
| Pre-Treatment | 29 | 14 | 4 | 0 | 0 | 0 | Total 69 mm diseased pockets |

-continued

| | 5 mm | 6 mm | 7 mm | 8 mm | 9 mm | 10 mm | |
|---|---|---|---|---|---|---|---|
| Post-Treatment | 1 | 0 | 0 | 0 | 0 | 0 | Total 1 mm diseased pockets |

This patient experienced 98% healing.

| 100% healed | |
|---|---|
| Furcation Involvement | Class II |
| Pre-Treatment | 2 |
| Post Treatment Class 0 | 2 |

Patient #6: Female, 42 Years Old Treated with Brand B Hydroxyapatite Paste

The patient was originally examined for beginning periodontal breakdown. Pockets were 4-5 mm with few 6 mm. With tissue damage isolated to soft tissue, the treatment plan was to reverse the initial tissue damage with improved hygiene to eliminate inflammation. This was successful and surgery was not indicated.

This patient became an example of what happens to the 94% of patients who do not floss. Her molars developed 5-9 mm requiring surgical intervention (no furcation damage)

The following table reports the number of pockets for each depth at pre-treatment, and results for patient #6 after-treatment with Brand B hydroxyapatite.

| | 5 mm | 6 mm | 7 mm | 8 mm | 9 mm | 10 mm | |
|---|---|---|---|---|---|---|---|
| Pre-Treatment | 5 | 1 | 4 | 1 | 3 | 0 | Total 38 mm diseased pockets |
| Post-Treatment | 0 | 0 | 0 | 0 | 0 | 0 | Total 0 mm diseased pockets |

This patient experienced 100% healing.

Patients #7: Brand C Hydroxyapatite Vs. Root Planing Vs. Brand A Hydroxyapatite

A group of Brand C patients and Root Planing patients were treated together. The results for these patients require a different approach from the presentations for Patients #1-#6. The objective was to compare the results for Patient #1 who was treated with Brand A, to results of Brand C vs. Root Planing.

Brand C patients & Root Planing patients began on an equal basis with identical preparatory procedures. All received similar hygiene training with monitoring. Root Planing was not done prior to treatment because it was one of the comparators. The goal for equitable conditions was achieved.

There were 61 Brand C patients, 60 Root Planing patients and 71 Brand A patients. The table below contains the average depth of the periodontal pockets for each group of patients prior to treatment. That average is called Initial Baseline. The Week 12 Result is the average depth of the periodontal pockets for each group of patients 12 weeks after treatment. The Depth Reduction is the difference between the Initial Baseline and the Week 12 Result.

|  | Brand C (N = 61) | Root Planing (N = 60) | Brand A (N = 71) |
|---|---|---|---|
| Initial Baseline | 5.3 | 5.4 | 6.02 |
| Week 12 Result | 3.69 | 3.68 | 3.09 |
| Depth Reduction | 1.61 | 1.72 | 2.94 |

The average depth reduction of 1.61 for treatment with Brand C hydroxyapatite is not significantly different from the average depth reduction of 1.72 for Root Planing. Therefore, treatment with Brand C hydroxyapatite only equaled Root Planing results in efficacy. Those results are significantly lower than the average depth reduction of 2.94 for patients treated with Brand A hydroxyapatite. This demonstrates that treatment with Brand C hydroxyapatite is not an improvement over standard root planing results and did not improve healing.

While we have described certain present preferred embodiments of our method for treating periodontal disease, it should be distinctly understood that the invention is not limited thereto but may be variously embodied within the scope of the following claims.

We claim:

1. A method of treating periodontal disease affecting at least one tooth surrounded by a periodontal pocket comprising placing in the periodontal pocket a composition consisting essentially of a fluid and hydroxyapatite particles, the fluid being water or saline, the hydroxyapatite particles having a normal particle size distribution, at least 90% of the hydroxyapatite particles having a particle size smaller than 50 $\mu$m and a particle size median of the hydroxyapatite particles being between 4 $\mu$m and 18.4 $\mu$m.

2. The method of claim 1 wherein a mean particle size of the hydroxyapatite particles is between 6 $\mu$m and 25 $\mu$m.

3. The method of claim 1 wherein the hydroxyapatite particles are crystalline.

4. The method of claim 1 wherein a sufficient amount of the fluid is present in the composition so that the composition is a paste.

5. The method of claim 1 wherein the fluid liquid and is present in a sufficient amount so that the composition is a gel.

6. The method of claim 1 wherein the composition is placed into the pocket by being injected through a syringe.

7. The method of claim 1 also comprising before placing the composition in the periodontal packet placing a sponge into a periodontal pocket to distend the pocket and to cause hemostasis and then removing the sponge.

8. The method of claim 7 wherein the sponge is impregnated with a material selected from the group consisting of epinephrine, alum, aluminum sulfate, aluminum, potassium sulfate, collagen, aluminum chloride, and oxy quinol sulfate.

9. The method of claim 7 wherein the sponge contains at least one antibacterial chemical.

10. The method of claim 9 wherein the antibacterial chemical is selected from the group consisting of peroxide, chlorhexidine, iodine and triiodomethane.

11. The method of claim 1 also comprising placing in the periodontal pocket a material selected from the group consisting of growth factors, nutrient factors, drugs, calcium containing compounds, anti-inflammatory agents, anti-microbial agents, root treatment materials, bone morphogenic proteins, dental matrix derivatives and combinations thereof.

* * * * *